(12) United States Patent
Stone

(10) Patent No.: US 6,383,732 B1
(45) Date of Patent: *May 7, 2002

(54) METHOD OF PREPARING XENOGRAFT HEART VALVES

(75) Inventor: Kevin R. Stone, Mill Valley, CA (US)

(73) Assignee: CrossCart, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,509

(22) Filed: Jun. 1, 2000

Related U.S. Application Data

(63) Continuation-in-part of application No. 09/248,476, filed on Feb. 11, 1999, now Pat. No. 6,231,608, and a continuation-in-part of application No. 09/248,336, filed on Feb. 11, 1999, now Pat. No. 6,267,786.

(51) Int. Cl.⁷ ............................... A01N 1/02; A61F 2/24
(52) U.S. Cl. ........................ 435/1.1; 623/2.1; 623/2.42; 435/325
(58) Field of Search ............................... 435/325, 1.01; 623/2.1, 2.42

(56) References Cited

U.S. PATENT DOCUMENTS

| | | | | |
|---|---|---|---|---|
| 4,034,418 A | 7/1977 | Jackson et al. | ............... | 3/1.911 |
| 4,344,193 A | 8/1982 | Kenny | ........................ | 3/1.911 |
| 4,400,833 A | 8/1983 | Kurland | ............................ | 3/1 |
| 4,502,161 A | 3/1985 | Wall | ............................ | 3/1.91 |
| 4,597,266 A | 7/1986 | Entrekin | ........................ | 62/46 |

(List continued on next page.)

FOREIGN PATENT DOCUMENTS

| | | |
|---|---|---|
| EP | 347496 | 12/1989 |
| WO | WO 84/03036 | 8/1984 |
| WO | WO 95/26740 | 10/1995 |
| WO | WO 95/28412 | 10/1995 |
| WO | WO 95/33828 | 12/1995 |

OTHER PUBLICATIONS

Spiro et al. "Occurrence of α–D–Galactosyl Residues in the Thyroglobulins from Several Species: Localization in the Saccharide Chains of the Complex Carbohydrate Units", J. Biol. Chem., 259, 9858–66 (1984).

Arumugham et al., "Structures of the Asparagine–Linked Sugar Chains of Laminin", Biochem. Biophys. Acta, 883, 112–26 (1986).

Good et al., "Identification of Carbohydrate Structures That Bind Human Antiporcine Antibodies: Implications for Discordant Xenografting in Man", Transplant. Proc., 24, 559–62 (1992).

Collins et al., "Cardiac Xenografts Between Primate Species Provide Evidence for the Importance of the α—Galactosyl Determinant in Hyperacute Rejection", J. Immunol., 154, 5500–10 (1995).

Hamadeh et al., "Human Natural Anti–Gal IgG Regulates Alternative Complement Pathway Activation on Bacterial Surfaces", J. Clin. Invest., 89, 1223–35 (1992).

Sandrin et al., "Anti–Pig IgM Antibodies in Human Serum React Predominantly with Gal α1–3 Gal Epitopes", Proc. Natl. Acad. Sci. USA, 90, 11391–95 (1993).

Morse, ed., Guide to Prosthetic Heart Valves, Springer–Verlag, New York, 225–232 (1985).

Galili et al., "Interaction Between Human Natural Anti–α—Galactosyl Immunoglobulin G and Bacteria of the Human Flora", Infect. Immun., 56, 1730–37 (1988).

Rodrigo et al., "Osteocartilaginous Allografts as Compared with Autografts in the Treatment of Knee Joint Osteocartilaginous Defects in Dogs", Clinical Orthopedics and Related Research, 134, pp. 342–349 (1978).

Sengupta et al., "The Fate of Transplants of Articular Cartilage in the Rabbit", The Journal of Bone and Joint Surgery, 56B, pp. 167–177 (1974).

Webber et al., "Cell Culture of Rabbit Meniscal Fibrochondrocytes: Proliferative and Synthetic Response to Growth Factors and Ascorbate", Journal of Orthopedic Research, 3, pp. 36–42 (1985).

Rubak et al., "Condrogenesis in Repair of Articular Cartilage Defects by Free Periosteal Grafts in Rabbits", Acta Orthop. Scand, 53, pp. 181–186 (1982).

Engkvist, Ove, "Reconstruction of Patellar Articular Cartilage with Free Autologous Perichondrial Grafts", Scand. J. Plast. Reconstr. Surg., 13, pp. 361–369 (1979).

Collins et al., "Characterization of Porcine Endothelial Cell Determinants Recognized by Human Natural Antibodies", Xenotransplantation, 1, pp. 36–46 (1994).

(List continued on next page.)

*Primary Examiner*—Sandra E. Saucier
*Assistant Examiner*—Vera Afremova
(74) *Attorney, Agent, or Firm*—McDermott, Will & Emery

(57) ABSTRACT

The invention provides an article of manufacture comprising a substantially non-immunogenic heart valve xenograft for implantation into humans. The invention further provides methods for preparing a heart valve xenograft by removing at least a portion of a soft tissue from a non-human animal to provide a xenograft; washing the xenograft in saline and alcohol; subjecting the xenograft to cellular disruption treatment; treating the xenograft with crosslinking agents, and digesting the xenograft with a proteoglycan-depleting factor and/or glycosidase. The invention also provides an article of manufacture produced by the above-identified method of the invention. The invention further provides a heart valve xenograft for implantation into a human including a portion of a heart valve from a non-human animal, wherein the portion has extracellular components and substantially only dead cells. The extracellular components have reduced proteoglycan molecules. Each of the xenografts of the invention are substantially non-immunogenic and have substantially the same mechanical properties as a corresponding native heart valve.

40 Claims, No Drawings

U.S. PATENT DOCUMENTS

| | | | |
|---|---|---|---|
| 4,609,627 A | 9/1986 | Goldstein | 435/269 |
| 4,627,853 A | 12/1986 | Campbell et al. | 623/16 |
| 4,642,120 A | 2/1987 | Nevo et al. | 623/16 |
| 4,678,470 A | 7/1987 | Nashef et al. | 623/16 |
| 4,755,593 A | 7/1988 | Lauren | 530/356 |
| 4,776,853 A | 10/1988 | Klement et al. | 8/94.11 |
| 4,789,663 A | 12/1988 | Wallace et al. | 514/21 |
| 4,801,299 A | 1/1989 | Brendel et al. | |
| 4,846,835 A | 7/1989 | Grande | 623/11 |
| 4,880,429 A | 11/1989 | Stone | 623/18 |
| 4,902,295 A | 2/1990 | Walthall et al. | 623/23.72 |
| 4,932,973 A | 6/1990 | Gendler | 623/16 |
| 5,007,934 A | 4/1991 | Stone | 623/20 |
| 5,067,962 A | 11/1991 | Campbell et al. | 623/16 |
| 5,071,741 A | 12/1991 | Brockband | 435/1 |
| 5,078,744 A | 1/1992 | Chvapil | 623/13 |
| 5,092,894 A | 3/1992 | Kenny | 623/18 |
| 5,116,374 A | 5/1992 | Stone | 623/16 |
| 5,131,850 A | 7/1992 | Brockband | 435/1 |
| 5,158,574 A | 10/1992 | Stone | 623/66 |
| 5,160,313 A | 11/1992 | Carpenter et al. | 600/34 |
| 5,171,273 A | 12/1992 | Silver et al. | 623/13 |
| 5,171,322 A | 12/1992 | Kenny | 623/18 |
| 5,171,660 A | 12/1992 | Carpenter et al. | 435/1 |
| 5,192,312 A | 3/1993 | Orton | 623/2 |
| 5,206,023 A | 4/1993 | Hunziker | 424/423 |
| 5,216,126 A | 6/1993 | Cox et al. | 530/350 |
| 5,263,984 A | 11/1993 | Li et al. | 623/15 |
| 5,306,304 A | 4/1994 | Gendler | 623/16 |
| 5,306,311 A | 4/1994 | Stone et al. | 623/18 |
| 5,333,626 A | 8/1994 | Morse et al. | 128/898 |
| 5,352,463 A | 10/1994 | Badylak et al. | 424/551 |
| 5,358,525 A | 10/1994 | Fox et al. | 623/18 |
| 5,507,810 A | 4/1996 | Prewett et al. | 623/11 |
| 5,516,532 A | 5/1996 | Atala et al. | 424/548 |
| 5,521,087 A | 5/1996 | Lee et al. | 435/240.2 |
| 5,613,982 A | 3/1997 | Goldstein | 623/11 |
| 5,632,778 A | 5/1997 | Goldstein | 623/11 |
| 5,782,915 A | 7/1998 | Stone | 623/11 |
| 5,863,296 A | 1/1999 | Orton | 623/15 |
| 5,865,849 A | 2/1999 | Stone | 623/18 |
| 5,899,937 A | 5/1999 | Goldstein | 623/2 |
| 5,902,338 A | 5/1999 | Stone | 623/13 |
| 5,904,716 A | 5/1999 | Gendler | 623/11 |
| 5,913,900 A | 6/1999 | Stone | 623/20 |
| 5,922,025 A | 7/1999 | Hubbard | 623/11 |
| 5,922,027 A | 7/1999 | Stone | 623/11 |
| 5,944,755 A | 8/1999 | Stone | 623/16 |
| 5,984,858 A | 11/1999 | Stone | 600/20 |
| 6,046,379 A | 4/2000 | Stone et al. | 623/11 |
| 6,049,025 A | 4/2000 | Stone et al. | 128/898 |
| 6,110,206 A | 8/2000 | Stone | 623/13.11 |
| 6,231,608 B1 * | 5/2001 | Stone | 623/16.11 |
| 6,267,786 B1 * | 7/2001 | Stone | 623/23.73 |

OTHER PUBLICATIONS

Satake et al., Limited Specificity of Xenoantibodies In Diabetic Patients Transplanted With Fetal Porcine Islet Cell Clusters. Main Antibody Reactivity Against ∀–linked Galactose–.

Containing Epitopes, Xenotransplanation, 1, pp. 89–101 (1994).

LaVecchio et al., "Enzymatic Removal of Alpha–Galactosyl Epitopes From Porcine Endothelial Cells Diminishes The Cytotoxic Effect of Natural Antibodies", Tansplantation, 60, pp. 841–847 (1995).

Stone et al., "Surgical Technique of Meniscal Replacement", Arthroscopy: The Journal of Arthroscopic and Related Surgery, 9, pp. 234–237 (1993).

Cotterell et al., "The Humoral Immune Response in Humans Following Cross–Perfusion of Porcine Organs", Transplantation, 60, pp. 861–868 (1995).

Galili, "Interaction of the Natural Anti–Gal Antibody with ∀–Galactosyl Epitopes: a Major Obstacle for Xenotransplantation in Humans", Immunology Today, 14, pp. 480–482 (1993).

Elves et al., "An Investigation Into The Immunogenicity Of Various Components of Osteoarticular Grafts", The British Journal of Experimental Pathology, 55, pp. 344–351 (1974).

Derby et al., "The Histochemical Specificity of Streptomyces Hyaluronidase and Chondroitinase ABC", Histochemical Journal, 10, pp. 529–547 (1978).

Homandberg et al., "High Concentrations of Fibronectin Fragments Cause Short–Term Catabolic Effects in Cartilage Tissue While Lower Concentrations Cause Continuous Anabolic Effects", Archives of Biochemistry and Biophysics, 311:2, pp. 213–218 (1994).

Homandberg et al., "Agents That Block Fibronectin Fragment–Mediated Cartilage Damage Also Promote Repair", Inflamm. Res., 46, pp. 467–471 (1997).

Homandberg et al., "Exposure of Cartilage to a Fibronectin Fragment Amplifies Catabolic Process while also Enhancing Anabolic Processes to Limit Damage", Journal of Orthopaedic Research, 16, pp. 237–246 (1998).

Homandberg et al., "Hyaluronic Acid Suppresses Fibronectin Fragment Mediated Cartilage Chondrolysis: I. In vitro", Osteoarthritis and Cartilage 5, pp. 309–319 (1997).

Homandberg et al., "Association of Proteoglycan Degradation with Catabolic Cytokine and Stromelysin Release from Cartilage Cultured with Fibronectin Fragments", 334:2, pp. 325–331 (1996).

Homandberg et al. "Fibronectin–Fragment–Induced Cartilage Chondrolysis is Associated with Release of Catabolic Cytokines", Biochem J. 321, pp. 751–757, (Great Britain) (1997).

Homandberg et al. "Cartilage Damaging Activities of Fibronectin Fragments Derived from Cartilage and Synovial Fluid", Osteoarthritis and Cartilage 6, pp. 231–244 (1998).

Homandberg et al., Cartilage Chondrolysis by Fibronectin Fragments Causes Cleavage of.

Aggrecan at the Same Site as Found in Osteoarthritic Cartilage, Osteoarthritis adn Cartilage 5, pp. 450–453 (1997).

Homandberg et al., "Fibronectin Fragment Mediated Cartilage Chondrolysis. I. Suppression by Anti–Oxidants", *BBA Biochimica et Biophysica Acta*, 1317, pp. 132–142 (1996).

Homandberg et al. "Fibronectin Fragment Mediated Cartilage Chondrolysis. II. Reparative Effects of Anti–Oxidants", *BBA Biochimica et Biophysica Acta*, 1317, pp. 143–148 (1996).

Kang et al., "Cultured Human Ankle and Knee Cartilage Differ in Susceptibility to Damage Mediated by Fibronectin Fragments", Journal of Orthopaedic Research, 16, pp. 551–556 (1998).

Lipman et al., "Xenografts of Articular Chondrocytes in the Nude Mouse", Calcif. Tissue Int., 35, pp. 767–772 (1983).

Oike et al. "Structural Analysis of Chick–embryo Cartilage Proteoglycan By Selective Degradation with Chondroitin Lyases (Chondroitinases) and Endo–∃–D–Galactsidase (Keratanase)", Biochem. J., 191, pp. 193–207 (1980).

Williams et al., "Hyaluronic Acid Suppresses Fibronectin Fragment Mediated Cartilage Chondrolysis: II. In vivo", Osteoarthritis and Cartilage, 5, pp. 235–240 (1997).

Zhu et al., "Viscoelastic Shear Properties of Aricular Cartilage and the Effects of Glycosidase Treatments", Journal of Orthopaedic Research, 11, pp. 771–781 (1993).

Ionescu et al., "Heart Valve Replacement with the Ionescu–Shiley Pericardial Xenograft", J. Thorac. Cardiovas. Surg., 73, pp. 31–42 (1977).

Stone et al., "Porcine and Bovine Cartilage Transplants in Cynomolgus Monkey: I. A Model for Chronic Xenograft Rejection", Transplantation, 63, pp. 640–645 (1997).

Galili et al., "Porcine and Bovine Cartilage Transplants in Cynomolgus Monkey: II. Changes in Anti–Gal Response During Chronic Rejection", Transplantation, 63, pp. 646–651 (1997).

Stedman's Medical Dictionary, Williams & Wilkins, 26 ed., pp. 793, 1966 (1995).

Galili et al., "Man, Apes, and Old World Monkeys Differ from Other Mammals in the Expression of α—Galactosyl Epitopes on Nucleated Cells", J. Biol. Chem., 263, 17755–17762 (1988)

Fadali et al., "The Use of Autogenous Peritoneum for Heart Valve Replacement", J. Thorac. Cardiovas. Surg., 60, pp. 188–195 (Aug. 1970).

Villa et al., "Residual Heteroantigenicity of Glutaraldehyde–Treated Porcine Cardiac Valves." *Tissue Antigens* 16: 62–69 (1980).

Chen et al., "Transgenic Porcine Valves Show No Signs of Delayed Cardiac Xenograft Rejection." *Annals of Thoracic Surgery* 71(5 Suppl.): S389–392 (May 2001).

* cited by examiner

METHOD OF PREPARING XENOGRAFT HEART VALVES

The present application is a continuation-in-part of U.S. patent application Ser. No. 09/248,476 filed Feb. 11, 1999, now U.S. Pat. No. 6,231,608 is also a continuation-in-part of U.S. patent application Ser. No. 09/248,336 filed Feb. 11, 1999, now U.S. Pat. No. 6,267,786.

FIELD OF THE INVENTION

The present invention relates to the field of treatment of defective human heart valves, and in particular, to replacement and repair of defective or damaged human heart valves using a substantially immunologically compatible heart valve from a non-human animal.

BACKGROUND OF THE INVENTION

Heart valves are composed of fibrochondrocytes and an extracellular matrix of collagen and elastic fibers, as well as a variety of proteoglycans. Various synthetic and tissue based materials (the latter either from the recipient organism or from a different organism within the same species) have been used for forming heart valve replacements. Each have their advantages and disadvantages.

In the case of synthetic heart valves, it may be possible to modify advantageously the properties of the heart valves by altering the monomers and/or the reaction conditions of the synthetic polymers. Synthetic heart valves may be associated with thromboembolism and mechanical failure, however. See U.S. Pat. No. 4,755,593.

Tissue based heart valves may demonstrate superior blood contacting properties relative to their synthetic counterparts. Tissue based heart valves also may be associated with inferior in vivo stability, however. See U.S. Pat. No. 4,755,593.

Pericardial xenograft tissue valves have been introduced as alternatives to the synthetic and the tissue based valves described above. See Ionescu, M. I. et al., Heart Valve Replacement With The Ionescu-Shiley Pericardial Xenograft, J. Thorac. Cardiovas. Surg. 73; 31–42 (1977). Such valves may continue to have calcification and durability problems, however. See Morse, D, ed. *Guide To Prosthetic Heart Valves*, Springer-Verlag, New York, 225–232 (1985).

Accordingly, there is a need for mechanically durable, flexible heart valves replacements which are capable of contacting the blood and are stable in vivo.

Much of the structure and many of the properties of original heart valves may be retained in transplants through use of heterograft or xenograft materials, that is, heart valve from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel xenografts are disclosed in WO 84/03036. However, none of these disclosures describe the use of a xenograft for heart valve replacement.

Once implanted in an individual, a xenograft provokes immunogenic reactions such as chronic and hyperacute rejection of the xenograft. The term "chronic rejection", as used herein, refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular matrices and/or extracellular components of the xenograft. For example, transplantation of heart valve xenografts from nonprimate mammals (e.g., porcine or bovine origin) into humans is primarily prevented by the interaction between the IgG natural anti-Gal antibody present in the serum of humans with the carbohydrate structure Galα1-3Galβ1-4G1cNAc-R (α-galactosyl or α-gal epitope) expressed in the xenograft. K. R. Stone et al., Porcine and bovine cartilage transplants in cynomolgus monkey: I. A model for chronic xenograft rejection, 63 Transplantation 640–645 (1997); U. Galili et al., Porcine and bovine cartilage transplants in cynomolgus monkey: II. Changes in anti-Gal response during chronic rejection, 63 Transplantation 646–651 (1997). In chronic rejection, the immune system typically responds within one to two weeks of implantation of the xenograft.

In contrast with "chronic rejection", "hyperacute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system, causing lysis of the vascular bed and stoppage of blood flow in the receiving individual within minutes to two to three hours.

The term "extracellular components", as used herein, refers to any extracellular water, collagen and elastic fibers, proteoglycans, fibronectin, elastin, and other glycoproteins, which are present in heart valve.

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic heart valve xenograft for implantation into a human in need of heart valve repair or replacement. The invention further provides methods for processing xenogeneic heart valve with reduced immunogenicity but with substantially native elasticity and load-bearing capabilities for xenografting into humans.

As used herein, the term "xenograft" is synonymous with the term "heterograft" and refers to a graft transferred from an animal of one species to one of another species. Stedman's Medical Dictionary, Williams & Wilkins, Baltimore, Md. (1995).

As used herein, the term "xenogeneic", as in, for example, xenogeneic heart valve, refers to heart valve transferred from an animal of one species to one of another species. Id.

The methods of the invention, include, alone or in combination, treatment with radiation, one or more cycles of freezing and thawing, treatment with a chemical cross-linking agent, treatment with alcohol or ozonation, and sterilization In addition to or in lieu of these methods, the methods of the invention include, alone or in combination, in any order, a cellular disruption treatment, glycosidase digestion of carbohydrate moieties of the xenograft, or treatment with proteoglycan-depleting factors. Optionally, the xenograft can be exposed to an aldehyde for further crosslinking. After one or more of the above-described processing steps, the methods of the invention provide a xenograft having substantially the same mechanical properties as a native heart valve.

As used herein, the term "cellular disruption" as in, for example, cellular disruption treatment, refers to a treatment for killing cells.

In one embodiment, the invention provides an article of manufacture comprising a substantially non-immunogenic heart valve xenograft for implantation into a human.

In another embodiment, the invention provides a method of preparing a heart valve xenograft for implantation into a human, which includes removing at least a portion of a heart valve from a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as a corresponding portion of a native heart valve.

In yet still a further embodiment, the invention provides a xenograft formed of a soft tissue for implantation into a human comprising a portion of the soft tissue from a nonhuman animal, wherein the portion includes a plurality of extracellular components, a plurality of substantially only dead cells, and an aldehyde in an amount ranging from about 0.01% to about 5% crosslinking a plurality of proteins of the extracellular components, the extracellular components and the dead cells having substantially no surface carbohydrate moieties which are susceptible to glycosidase digestion, and whereby the portion is substantially non-immunogenic and has substantially the same mechanical properties as a corresponding portion of the native soft tissue, and wherein the soft tissue is suitable for use as heart valve xenograft material.

As used herein, the term "portion" refers to all or less than all of the respective soft tissue heart valve xenograft material. "Soft tissue xenograft material" refers to the non-human heart valves, valve portions, such as leaflets, and other soft tissue materials that can be fashioned into valves and valve portions, such as, for example, pericardium.

In another embodiment, the invention provides a method of preparing a heart valve xenograft for implantation into a human, which includes removing at least a portion of a heart valve from a non-human animal to provide a xenograft; washing the xenograft in water and alcohol; subjecting the xenograft to a cellular disruption treatment; and digesting the xenograft with a glycosidase to remove surface carbohydrate moieties, whereby the xenograft has substantially the same properties as a corresponding portion of a native heart valve. As used herein, the term "surface carbohydrate moiety (moieties)" refers to a terminal α-galactosyl sugar at the non-reducing end of a carbohydrate chain.

In a further embodiment, the invention provides a method of preparing a heart valve xenograft for implantation into a human, which includes removing at least a portion of heart valve from a non-human animal to provide a xenograft; washing the xenograft in water and alcohol; subjecting the xenograft to a cellular disruption treatment; and digesting the xenograft with a proteoglycan-depleting factor to remove at least a portion of the proteoglycans from the xenograft, whereby the xenograft has substantially the same mechanical properties as a corresponding portion of a native heart valve and is substantially non-immunogemc.

In yet further embodiments, the invention provides articles of manufacture including substantially non-immunogenic heart valve xenografts for implantation into humans produced by one or more of the above-identified methods of the invention.

In another embodiment, the invention provides a heart valve xenograft for implantation into a human which includes a portion of a heart valve from a non-human animal, wherein the portion has substantially no surface carbohydrate moieties which are susceptible to glycosidase digestion, and whereby the portion has substantially the same mechanical properties as a corresponding portion of a native heart valve. In still yet another embodiment, the invention provides a heart valve xenograft for implantation into a human which includes a portion of a heart valve from a non-human animal, wherein the portion includes extracellular components and substantially only dead cells, the extracellular components having reduced proteoglycans. The portion of the heart valve is substantially non-immunogenic and has substantially the same mechanical properties as the native heart valve.

DETAILED DESCRIPTION OF THE PREFERRED EMBODIMENTS

The present invention is directed against the chronic rejection of xenografts for implantation into humans. Accordingly, heart valve xenografts produced in accordance with the methods of the invention are substantially non-immunogenic, while generally maintaining the mechanical properties of a native heart valve.

While the heart valve may undergo some shrinkage during processing, a heart valve xenograft prepared in accordance with the invention will have the general appearance of a native heart valve xenograft. For example, a mitral valve xenograft prepared in accordance with the invention will have the general appearance of a native mitral valve, and semi-lunar valve xenografts of the invention will have the general appearance of a native semi-lunar valves. The heart valve xenograft may be valve segments, such as individual leaflets, each of which may be implanted into receipient heart.

The invention provides, in one embodiment, a method for preparing or processing a xenogeneic heart valve for engraftment into humans. The heart valve may be harvested from any non-human animal to prepare the xenografts of the invention. Heart valve from transgenic non-human animals or from genetically altered non-human animals may also be used as xenografts in accordance with the present invention. Preferably, bovine, ovine, or porcine hearts, and more preferably porcine hearts, serve as sources of heart valves used to prepare the xenografts. Alternatively, porcine pericardium can be used to form the heart valve xenografts of the present invention.

In the first step of the method of the invention, an intact heart is removed from a non-human animal. Suitable heart valve tissues are excised from the heart. Pericardium may be also harvested and implanted to replace or repair damaged heart valves by those of skill in the art using known techniques. Preferably heart valve from a corresponding heart valve is used to make the heart valve xenograft of the invention. For example, mitral valve may be used to make a mitral valve xenograft for implantation.

In accordance with the invention, the heart which serves as the source of the heart valve is collected from freshly killed animals and preferably immediately placed in a suitable sterile isotonic or other tissue preserving solution. Preferably, harvesting of the hearts and valves occurs as soon as possible after slaughter of the animal and preferably is performed in the cold, i.e., in the approximate range of about 5° C. to about 20° C., to minimize enzymatic degradation of the heart valve, under strict sterile technique.

The harvested valves and tissue are dissected free of adjoining tissue. Alternatively, a valve may be dissected with portions of the surrounding cardiac tissue. For example, tricuspid valves are excised as separate leaflets, or as an intact valve including the fibrous ring surrounding the auriculo-ventricular orifice and the tendinous chords. Once removed, optionally, the valve or valve portions are supported with stents, rings and the like. The heart valve or portion is carefully identified and dissected free of adhering tissue, plaques, calcifications and the like, thereby forming the xenograft.

In one form of the invention, porcine peritoneum or pericardium is harvested to form a heart valve xenografts according to procedures known to those of ordinary skill in the art. See, for example, the peritoneum harvesting procedure discussed in U.S. Pat. No. 4,755,593 by Lauren.

In a preferred form of the invention, the xenograft is then washed in about ten volumes of sterile cold water to remove residual blood proteins and water soluble materials. The xenograft is then immersed in alcohol at room temperature for about five minutes, to sterilize the tissue and to remove non-collagenous materials. After alcohol immersion, the xenograft may be directly implanted or may be subjected to at least one of the following treatments: radiation treatment, treatment with alcohol, ozonation, one or more cycles of freezing and thawing, and/or treatment with a chemical cross-linking agent. When more than one of these treatments is applied to the xenograft, the treatments may occur in any order.

In one embodiment of the method of the invention, the xenograft is treated by exposure to ultraviolet radiation for about fifteen minutes or gamma radiation in an amount of about 0.5 to 3 MegaRad.

In another embodiment, the xenograft is treated by again being placed in an alcohol solution. Any alcohol solution may be used to perform this treatment. Preferably, the xenograft is placed in a 70% solution of isopropanol at room temperature.

In still another embodiment, the xenograft is subjected to ozonation.

In a further embodiment of the method of the invention, the xenograft is treated by freeze/thaw cycling. For example, the xenograft may be frozen using any method of freezing, so long as the xenograft is completely frozen, i.e., no interior warm spots remain which contain unfrozen heart valve tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes. No external heat or radiation source is used, in order to minimize fiber degradation.

In yet a further embodiment, the xenograft optionally is exposed to a chemical agent to tan or crosslink the proteins within the extracellular components, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, may be used to crosslink the extracellular collagen of the xenograft in accordance with the method of the invention. Other suitable crosslinking agents include aliphatic and aromatic diamines, carbodiimides, diisocyanates, and the like.

When an aldehyde such as, for example, glutaraldehyde is used as the crosslinking agent, the xenograft may be placed in a buffered solution containing about 0.001% to about 5.0% glutaraldehyde and preferably, about 0.01 % to about 5.0% glutaraldehyde, and having a pH of about 7.4. More preferably about 0.01% to about 0.10% aldehyde, and most preferably about 0.01% to about 0.05% aldehyde is used. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from one to five days, and most preferably from three to five days.

Alternatively, the xenograft can be exposed to a crosslinking agent in a vapor form, including, but not limited to, a vaporized aldehyde crosslinking agent, such as, for example, vaporized formaldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.001% to about 5.0% and preferably, about 0.01% to about 5.0%, and a pH of about 7.4. More preferably, the xenograft is exposed to the aldehyde in an amount ranging from about 0.01% to about 0.10%, and most preferably to an aldehyde ranging in an amount from about 0.01% to about 0.05%. The xenograft is exposed to the aldehyde for a period of time which can be from one to fourteen days, and preferably from one to five days, and most preferably from three to five days. Exposure to vaporized crosslinking agent can result in reduced residual chemicals in the xenograft from the crosslinking agent exposure.

The crosslinking reaction continues until the immunogenic determinants are substantially eliminated from the xenogeneic heart valve, but the reaction is terminated prior to significant alterations of the mechanical properties of the xenograft. When diamines are also used as crosslinking agents, the glutaraldehyde crosslinking occurs after the diamine crosslinking, so that any unreacted diamines are capped. After the crosslinking reactions have proceeded to completion as described above, the xenograft is rinsed to remove residual chemicals, and 0.01–.10 M glycine, and preferably, 0.01–0.05 M glycine is added to cap any unreacted aldehyde groups which remain.

In addition to the above treatments, the xenograft is subjected to a cellular disruption treatment to kill the xenograft's cells. The cellular disruption treatment precedes or follows digestion of the xenograft with glycosidases to remove surface carbohydrate moieties from the xenograft. In addition or in lieu of the glycosidase treatment, either preceding or following the glycosidase treatment, the xenograft may be treated with proteoglycan-depleting factors.

The xenograft is subjected to a cellular disruption treatment to kill the cells of the heart valve. Typically after surface carbohydrate moieties have been removed from living cells and the extracellular components, the living cells reexpress the surface carbohydrate moieties. Reexpression of antigenic moieties of a xenograft can provoke continued immunogenic rejection of the xenograft. In contrast, dead cells are unable to reexpress surface carbohydrate moieties. Removal of antigenic surface carbohydrate moieties from dead cells and the extracellular components of a xenograft substantially permanently eliminates antigenic surface carbohydrate moieties as a source of immunogenic rejection of the xenograft.

Accordingly, in the above-identified embodiments, the xenograft of the present invention is subjected to freeze/thaw cycling as discussed above to disrupt, i.e., to kill the cells of the heart valve. Alternatively, the xenograft of the present invention is treated with gamma radiation having an amount of 0.2 MegaRad up to about 3 MegaRad. Such radiation kills the heart valve cells and sterilizes the xenograft. Once killed, the heart valve cells are no longer able to reexpress antigenic surface carbohydrate moieties such α-gal epitopes which are factors in the immunogenic rejection of the transplanted xenografts.

Either before or after the heart valve cells are killed, in embodiments of the invention, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

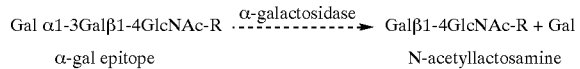

$$\text{Gal }\alpha\text{1-3Gal}\beta\text{1-4GlcNAc-R} \xrightarrow{\alpha\text{-galactosidase}} \text{Gal}\beta\text{1-4GlcNAc-R + Gal}$$

α-gal epitope            N-acetyllactosamine

The N/acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammals and in New World monkeys (monkeys of South America) as $1\times10^6$–$35\times10^6$ epitopes per cell, as well as on macromolecules such as proteoglycans of the extracellular components. U. Galili et al., Man, apes, and Old World monkeys differ from other mammals in the expression of α-galactosyl epitopes on nucleated cells, 263 J. Biol. Chem. 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., Interaction between human natural anti-α-galactosyl immunoglobulin G and bacteria of the human flora, 56 Infect. Immun. 1730 (1988); R. M. Hamadeh et al., Human natural anti-Gal IgG regulates alternative complement pathway activation on bacterial surfaces, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., Interaction of the natural anti-Gal antibody with α-galactosyl epitopes: A major obstacle for xenotransplantation in humans, 14 Immunology Today 480 (1993); M. Sandrin et al., Anti-pig IgM antibodies in human serum react predominantly with Galα1-3Gal epitopes, 90 Proc. Natl. Acad. Sci. USA 11391 (1993); H. Good et al., Identification of carbohydrate structures which bind human anti-porcine antibodies: implications for discordant grafting in man. 24 Transplant. Proc. 559 (1992); B. H. Collins et al., Cardiac xenografts between primate species provide evidence for the importance of the α-galactosyl determinant in hyperacute rejection, 154 J. Immunol. 5500 (1995). Furthermore, xenotransplantation results in major activation of the immune system to produce increased amounts of high affinity anti-Gal. In accordance with the invention, the substantial elimination of α-gal epitopes from cells and from extracellular components of the xenograft, and the prevention of reexpression of cellular α-gal epitopes diminish the immune response against the xenograft associated with anti-Gal antibody binding with α-gal epitopes.

In addition, the heart valve xenografts of the invention may be treated with polyethylene glycol (PEG) prior to or concurrently with treatment with glycosidase. PEG acts as a carrier for the glycosidase by covalently bonding to the enzyme and to the collagen extracellular components. Further, PEG-treated xenografts reduce immunogenicity.

Either before or after the xenograft cells are killed, in embodiments of the invention, the xenograft is washed or digested with one or more different types of proteoglycan-depleting factors. The proteoglycan-depleting factor treatment can precede or follow glycosidase treatment. Proteoglycans such as glycosaninoglycans (GAGs) are interspersed either uniformly as individual molecules or within varying amounts within the extracellular components of the present invention's xenograft. The GAGs include mucopolysaccharide molecules such as chondroitin 4-sulfate, chondroitin 6-sulfate, keratan sulfate, dermatan sulfate, heparin sulfate, hyaluronic acid, and mixtures thereof. The proteoglycans including such GAGs contain attached carbohydrates such as α-gal epitopes. Such epitopes stimulate an immune response once the xenograft is transplanted, as discussed above. Washing or digesting the xenograft with the proteoglycan-depleting factor removes at least a portion of the proteoglycans and attached α-gal epitopes from the extracellular components of the xenograft, and thereby diminishes the immune response against the xenograft upon its transplantation. After the proteoglycan-depleting factor treatment and subsequent transplantation, natural tissue repopulates the remaining collagen shell.

Non-limiting examples of the proteoglycan-depleting factors used in the present invention include proteoglycan-depleting factors such as chondroitinase ABC, hyaluronidase, chondroitin AC II lyase, keratanase, trypsin, fibrinectin and fragments of fibronectin.

Other proteoglycan-depleting factors known to those of ordinary skill in the art are also possible for use with the present invention, however. The present invention's xenograft is treated with proteoglycan-depleting factor in an amount effective for removing at least a portion of the proteoglycans from the extracellular components of the xenograft. Preferably, the xenograft is treated with proteoglycan-depleting factor such as hyaluronidase in an amount ranging from about 1.0 TRU/ml to about 100.0 TRU/ml or proteoglycan-depleting factor such as chondroitinase ABC in an amount ranging from about 0.01 u/ml to about 2.0 u/ml or most preferably, in an amount ranging from about 1.0 ul/ml to about 2.0 u/ml. The xenograft can also be treated with proteoglycan-depleting factor such as fibronectin fragment, (e.g., amino terminal 29-kDa fibronectin fragment) in an amount ranging from about .01 $\mu$M to about 1.0 $\mu$M, and preferably in an amount ranging from about 0.1 $\mu$M to about 1.0 $\mu$M.

Prior to treatment, the xenograft optionally may be pierced to increase permeability to agents used to render the xenograft substantially non-immunogenic. A sterile surgical needle such as an 18 gauge needle is used to perform this piercing step, or, alternatively a comb-like apparatus containing a plurality of needles are used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the surface of the xenograft.

Prior to implantation, the heart valve xenograft of the invention may be treated with limited digestion by proteolytic enzymes such as ficin or trypsin to increase tissue flexibility, or coated with anticalcification agents, antithrombotic coatings, antibiotics, growth factors, or other drugs which may enhance the incorporation of the xenograft into the recipient. The heart valve xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

The heart valve xenograft of the invention, or a segment thereof, may be implanted into damaged human hearts by those of skill in the art using known surgical techniques, for example, by open heart surgery, or minimally invasive techniques such as endoscopic surgery, and transluminal implantation. Specific instruments for performing such surgical techniques are known to those of skill in the art, which ensure accurate and reproducible placement of heart valve implants.

EXAMPLE 1

Assay For $\alpha$-Gal Epitopes' Elimination From Heart valve By $\alpha$-Galactosidase In this example, an ELISA assay for assessing the elimination of $\alpha$-gal epitopes from heart valve is conducted.

A monoclonal anti-Gal antibody (designated M86) which is highly specific for $\alpha$-gal epitopes on glycoproteins is produced by fusion of splenocytes from anti-Gal producing knock-out mice for $\alpha$1,3 galactosyltransferase, and a mouse hybridoma fusion partner.

M86 binds to synthetic $\alpha$-gal epitopes linked to bovine serum albumin (BSA), to bovine thyroglobulin which has 11 $\alpha$-gal epitopes, R. G. Spiro et al., Occurrence of $\alpha$-D-galactosyl residues in the thyroglobulin from several species. Localization in the saccharide chains of complex carbohydrates, 259 J. Biol. Chem. 9858 (1984); or to mouse laminin which has 50 $\alpha$-gal epitopes, R. G. Arumugham et al., Structure of the asparagine-linked sugar chains of laminin. 883 Biochem. Biophys. Acta 112 (1986); but not to human thyroglobulin or human laminin, Gal$\beta$1-4 G1cNAc-BSA (N-acetyllactosamine-BSA) and Gal$\alpha$1-4Gal$\beta$1-4G1cNAc-BSA (P1 antigen linked to BSA), all of which completely lack $\alpha$-gal epitopes. Binding is measured at different dilutions of the M86 tissue culture medium.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with fragments of heart valve xenograft material about 5 $\mu$m to about 100 $\mu$m in size, and more preferably with heart valve fragments ranging from about 10 $\mu$m to about 50 $\mu$m in size, at various heart valve xenograft material concentrations ranging from about 200 mg/ml to about 1.5 mg/ml. Subsequently, the xenograft fragments are removed by centrifugation at centrifugation rate ranging from about 20,000×g to about 50,000×g. The proportion of M86 bound to the xenograft is assessed by measuring the remaining M86 activity in the supernatant, in ELISA with $\alpha$-gal-BSA as described in the prior art in, for example, U. Galili et al., Porcine and bovine cartilage transplants in cynomolgus monkey: II. Changes in anti-Gal response during chronic rejection, 63 Transplantation 645–651 (1997). The extent of binding of M86 to the heart valve material is defined as a percentage inhibition of subsequent binding to, $\alpha$-gal-BSA. There is a direct relationship between the amount of $\alpha$-gal epitopes in the heart valve material and the proportion of M86 complexed with the heart valve material fragments, thus removed from the supernatant (i.e., percentage inhibition).

To perform the assay, fragments of homogenized heart valve xenograft treated with $\alpha$-galactosidase are incubated with the M86 monoclonal antibody (diluted 1:100) for 20 hr at 4° C. Subsequently, the xenograft tissue fragments are removed by centrifugation at 35,000×g and the remaining M86 in the supernatant is assessed in ELISA with $\alpha$-gal-BSA as solid phase antigen. The heart valve xenograft tissue is treated with 200 U/ml $\alpha$-galactosidase for 4 hour at 30° C. followed by five washes with phosphate-buffered solution (PBS), which completely eliminates the $\alpha$-gal epitopes.

EXAMPLE 2

Assessment Of Primate Response To Implanted Porcine Heart Valve Xenografts Treated With $\alpha$-Galactosidase In this example, porcine peritoneum heart valve implants are treated with $\alpha$-galactosidase to eliminate $\alpha$-galactosyl epitopes, the implants are transplanted into cynomolgus monkeys, and the primate response to the heart valve implants is assessed.

Porcine peritoneum is harvested for forming heart valve xenografts and adherent fatty and/or muscular tissues surgically removed. The specimens are washed for at least five minutes with an alcohol, such as ethanol or isopropanol, to remove lipid soluble contaminants. The heart valve specimens are frozen at a temperature ranging from about −35° C.

to about −90° C., and preferably at a temperature up to about −70° C., to disrupt, that, is to kill, the specimens' fibrochondrocytes.

Each xenograft specimen is cut into two portions. Each first portion is immersed in a buffer solution containing α-galactosidase at a predetermined concentration. The specimens are allowed to incubate in the buffer solutions for a predetermined time period at a predetermined temperature. Each second portion is incubated under similar conditions as the corresponding first portion in a buffer solution in the absence of α-galactosidase and serves as the control.

At the end of the incubation, the heart valve xenograft specimens are washed under conditions which allow the enzyme to diffluse out. Assays are performed to confirm the complete removal of the α-gal epitopes.

The porcine peritoneum is formed into heart valves and the heart valve xenograft specimens are implanted in the six cynomolgus monkeys according to heart valve implantation procedures known to those of ordinary skill in the art.

The implantation procedures are performed under sterile surgical technique, and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-soft tissue antibodies (i.e., antibodies binding to soft tissue antigens other than the α-gal epitopes) in serum samples from the transplanted monkeys. At least two blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-soft tissue antibody activity.

Anti-Gal activity is determined in the serum samples in ELISA with α-gal-BSA as solid phase antigen, according to methods known in the prior art, such as, for example, the methods described in Galili et al., Porcine and bovine cartilage transplants in cynomolgus monkey: II. Changes in anti-Gal response during chronic rejection, 63 Transplantation 645–651 (1997).

Assays are conducted to determine whether α-galactosidase treated xenografts induce the formation of anti-soft tissue antibodies. For measuring anti-soft tissue antibody activity, ELISA assays are performed according to methods known in the prior art, such as, for example, the methods described in K. R. Stone et al., Porcine and bovine cartilage transplants in cynomolgus monkey: I. A model for chronic xenograft rejection, 63 Transplantation 640–645 (1997).

The heart valve xenograft specimens are optionally explanted at one to two months post-transplantation, sectioned and stained for histological evaluation of inflammatory infiltrates. Post-transplantation changes in anti-Gal and other anti- soft tissue antibody activities are correlated with the inflammatory histologic characteristics (i.e., granulocytes or mononuclear cell infiltrates) within the explanted heart valve, one to two months post-transplantation, using methods known in the art, as, for example, the methods described in K. R. Stone et al., Porcine and bovine cartilage transplants in cynomolgus monkey: I. A model for chronic xenograft rejection, 63 Transplantation 640–645 (1997).

Where the heart valve is explanted, the heart valve xenografts are aseptically harvested, using anesthetic procedure, removal of the implants and closure of the soft tissues (where the animals are allowed to recover). At the time of the xenograft removal, fluid, if present in amounts sufficient to aspirate, is collected from the for possible immunologic testing if the gross and histopathologic evaluation of the transplants indicate good performance of the transplanted heart valve xenograft material.

The animals which have had xenograft implantations are allowed to recover and are monitored closely until the incisions have healed and the gait is normal. The xenograft samples are collected, processed, and examined microscopically.

Portions of the heart valve implants and surrounding tissues are frozen in embedding mediums for frozen tissue specimens in embedding molds for immunohistochemistry evaluation according to the methods known in the prior art. "TISSUE-TEK®" O.C.T. compound which includes about 10% w/w polyvinyl alcohol, about 4% w/w polyethylene glycol, and about 86% w/w nonreactive ingredients, and is manufactured by Sakura FinTek, Torrence, California, is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 3

Assessment Of Primate Response To Implanted Heart Valve Xenografts Subjected To Freeze Thaw Cycling And Treatment With Proteoglycan-Depleting Factors.

In this example, porcine peritoneum soft tissue heart valve implants are prepared and frozen to disrupt, that is, to kill the specimens' cells, as described above in Example 2. The heart valve implants are further treated with proteoglycan-depleting factors to eliminate substantially the proteoglycans from the xenograft. Subsequently, the xenografts are treated with glycosidase to remove substantially remaining α-gal epitopes from the xenograft, as described in Example 2. Substantial elimination of the proteoglycans and the remaining α-gal epitopes interferes with the ability of the recipient subject's immune system to recognize the xenograft as foreign. The heart valve implants are transplanted into cynomologous monkeys, and the primate response to the heart valve implants is assessed.

Heart valve implants from porcine peritoneum are prepared following the preparation procedures outlined in Example 2 including the sterilization, and freeze/thaw cycling treatments. A chondroitinase ABC solution is then prepared by combining 0.05M Tris-HCL (7.88 gm/liter-MW=157.60), 5 mM benzamidine-HCL (0.783 gm/liter-MW=156.61), 0.010 M N-ethylmaleimide (1.2513 gm/liter-MW=125.13), and 0.001M phenylmethylsulfonyl fluoride (0.17420 gm/liter-MW=174.2), dissolved in methanol. A mixture of 0.15 M NaCl (8.775 gm/liter-MW=58.5), penicillin and streptomycin (1% (v/v) 10 ml/liter) along with enzyme in the amount of 1 unit chondroitinase ABC (Sigma #C-3509) Enzyme Solution per 1 ml of solution is added to bring the solution to 1 liter.

Each heart valve xenograft specimen is incubated in the chondroitinase ABC enzyme solution at a concentration of 1 ml of solution per a 3 mm diameter heart valve plug. The incubations are performed at a pH of 8.0 and 37 degrees C in a shaker water bath for 48 hours. After the incubation, each heart valve specimen is washed in appropriate buffer and the washings are added to the chondroitinase ABC solution. Each heart valve specimen is then re-incubated with the chondroitinase ABC solution at a concentration of 1 unit chondroitinase ABC (Sigma #C-3509) Enzyme Solution per 1 ml of solution for another 48 hours as described above. Each heart valve specimen is again washed in appropriate buffer solution, and the washings are added to the chondroitinase ABC solution.

Each heart valve specimen is then incubated in 1 ml of trypsin solution (1 mg/nil trypsin, 0.15 M NaCl, 0.05 M Na Phosphate) at a pH of 7.2 for 24 hours. The incubation is performed in a shaker water bath at 37 degrees C. Each heart valve specimen is washed in appropriate buffer solution, and the washings are added to the trypsin solution.

Each specimen is then placed in 1 ml of hyaluronidase solution (0.01 mg/ml testicular hyaluronidase, 0.005 M Benzamidine HCL, 001 M PMSF, 0.010M Nethylmaleimide, 0.005 M Benzamidine HCL, 1% v/v penicillin and streptomycin) at a pH 6.0 for 24 hours. The incubation is performed in a shaker water bath at 37 degrees C. Each heart valve specimen is then rinsed again in an appropriate buffer solution, and the washings are added to the hyaluronidase solution.

Subsequently, the implants are treated with glycosidase as described above in Example 2, implanted into the monkeys, and the occurrence of an immune response against each of the xenografts is assessed as described above in Example 2.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a xenograft heart valve for implantation into a human, which comprises
    a. removing at least a portion of a heart valve from a non-human animal to provide a xenograft;
    b. washing the xenograft in water and alcohol;
    c. subjecting the xenograft to a cellular disruption treatment; and
    d. treating the xenograft with a glycosidase to remove a plurality of first surface carbohydrate moieties,
    whereby the xenograft is substantially non-immunogenic and has substantially the same mechanical properties as the native heart valve.

2. A method according to claim 1, wherein the glycosidase is a galactosidase.

3. The method of claim 2, wherein the galactosidase is an α-galactosidase.

4. The method of claim 1, further comprising the step of depleting substantially a plurality of proteoglycans from the xenograft.

5. The method of claim 4, wherein the depleting step comprises digesting the xenograft with at least one proteoglycan-depleting factor selected from the group consisting of chondroitinase ABC, hyaluronidase, chondroitin AC II lyase, keratanase, trypsin and fibronectin fragment.

6. The method of claim 1, further comprising the step of: after step c, piercing the xenograft.

7. The method of claim 1, further comprising the step of: after step c, treating the xenograft with at least one enzyme.

8. The method of claim 7, wherein the enzyme is selected from the group consisting of ficin and trypsin.

9. The method of claim 1, further comprising the step of: after step c, treating the xenograft with one or more agents selected from the group consisting of anticalcification agents, antithrombotic agents, antibiotics, and growth factors.

10. The method of claim 1, further comprising the step of: after step c, sterilizing the xenograft.

11. The method of claim 10, wherein the sterilizing step comprises sterilizing the xenograft with one or more agents selected from the group consisting of ethylene oxide, and propylene oxide.

12. The method of claim 1, further comprising the step of: after step c, treating the xenograft with at least one crosslinking agent.

13. The method of claim 12, wherein the crosslinking agent is selected from the group consisting of aldehydes, aromatic diamines, carbodiimides, and diisocyanates.

14. The method of claim 13, wherein at least one crosslinking agent is glutaraldehyde.

15. The method of claim 14, wherein the xenograft is crosslinked using a solution containing about 0.01 percent to about 5 percent glutaraldehyde.

16. The method of claim 4, further comprising the step of: after step c, treating the xenograft with at least one crosslinking agent.

17. The method of claim 16, wherein the crosslinking agent is selected from the group consisting of aldehydes, aromatic diamines, carbodiimides, and diisocyanates.

18. The method of claim 17, wherein at least one crosslinking agent is glutaraldehyde.

19. The method of claim 18, wherein the xenograft is crosslinked using a solution containing about 0.01 percent to about 5 percent glutaraldehyde.

20. The method of claim 1, further comprising the step of: after step c, treating the xenograft with polyethylene glycol.

21. The method of claim 1, further comprising the step of: after step c, exposing the xenograft to a crosslinking agent in a vapor form.

22. The method of claim 1, wherein the cellular disruption treatment comprises freeze/thaw cycling.

23. The method of claim 1, wherein the cellular disruption treatment comprises exposure to gamma radiation.

24. An article of manufacture comprising a substantially non-immunogenic, heart valve xenograft for implantation into a human, produced by
    a. removing at least a portion of a heart valve from a non-human animal to provide a xenograft;
    b. washing the xenograft in water and alcohol;
    c. subjecting the xenograft to a cellular disruption treatment; and
    d. treating the xenograft with a glycosidase to remove a plurality of first surface carbohydrate moieties, whereby the xenograft is substantially non-immunogenic and has substantially the same mechanical properties as the native heart valve.

25. The article of manufacture of claim 24, wherein the glycosidase is a galactosidase.

26. The article of manufacture of claim 25, wherein the galactosidase is an α-galactosidase.

27. The article of manufacture of claim 24, further comprising the step, after step c, of digesting the xenograft with a proteoglycan-depleting factor to remove substantially a plurality of proteoglycans from the xenograft.

28. The article of manufacture of claim 27, wherein the proteoglycan-depleting factor is selected from the group consisting of chondroitinase ABC, hyaluronidase, chondroitin AC II lyase, keratanase, trypsin and fibronectin fragment.

29. The article of manufacture of claim 24, further comprising the step, after step b, of creating a plurality of punctures into the xenograft for increasing permeability to agents and enzymes.

30. The article of manufacture of claim 24, further comprising treating the xenograft with one or more agents selected from the group consisting of anticalcification agents, antithrombotic agents, antibiotics, and growth factors.

31. The article of manufacture of claim 24, further comprising sterilizing the xenograft.

32. The article of manufacture of claim 24, further comprising treating the xenograft with polyethylene glycol.

33. The article of manufacture of claim 24, further comprising, after step c, treating the xenograft with a crosslinking agent.

34. The article of manufacture of claim 33, wherein the crosslinking agent is an aldehyde.

35. The article of manufacture of claim 34, wherein the aldehyde is glutaraldehyde.

36. The article of manufacture of claim 27, further comprising, after step c, treating the xenograft with a crosslinking agent.

37. The article of manufacture of claim 36, wherein the crosslinking agent is selected from the group consisting of aldehydes, aromatic diamines, carbodiimides, and diisocyanates.

38. The article of manufacture of claim 37, wherein the aldehyde is glutaraldehyde.

39. The article of manufacture of claim 24, further comprising the step of after step b, freezing and thawing the xenograft.

40. The article of manufacture of claim 24, further comprising the step of treating the xenograft with gamma-radiation.

* * * * *